US010357369B2

(12) United States Patent
Leung et al.

(10) Patent No.: US 10,357,369 B2
(45) Date of Patent: Jul. 23, 2019

(54) METHOD FOR PRODUCING KNEE REPLACEMENT IMPLANT AND IMPLANT FOR KNEE REPLACEMENT

(71) Applicants: Shandong Weigao Orthopaedic Device Co. Ltd., Weihai (CN); The Chinese University of Hong Kong, Hong Kong (CN); Shenzhen Institutes of Advanced Technology, Chinese Academy of Science., Shenzhen (CN)

(72) Inventors: Kwok-Sui Leung, Hong Kong (CN); Wing-Hoi Cheung, Hong Kong (CN); Jianghui Qin, Nanjing (CN); Chun-Sing Chui, Hong Kong (CN); Dufang Shi, Jiujiang (CN); Kwoon-Ho Chow, New Territories (HK); Ling Qin, Hong Kong (CN); Wanfu Kou, Weihai (CN); Chenglin Lu, Weihai (CN)

(73) Assignees: Shandong Weigao Orthopaedic Device Co. Ltd., Weihai (CN); The Chinese University of Hong Kong, Hong Kong (CN); Shenzhen Institutes of Advanced Technology, Chinese Academy of Science, Shenzhen (CN)

( * ) Notice: Subject to any disclaimer, the term of this patent is extended or adjusted under 35 U.S.C. 154(b) by 40 days.

(21) Appl. No.: 15/228,841

(22) Filed: Aug. 4, 2016

(65) Prior Publication Data
US 2018/0036128 A1   Feb. 8, 2018

(51) Int. Cl.
A61F 2/38   (2006.01)
A61F 2/32   (2006.01)
(Continued)

(52) U.S. Cl.
CPC .......... *A61F 2/30942* (2013.01); *A61F 2/389* (2013.01); *A61F 2/3859* (2013.01);
(Continued)

(58) Field of Classification Search
CPC ... A61B 34/10; A61B 34/20; A61B 2034/105; A61B 2034/107; A61B 2034/2055;
(Continued)

(56) References Cited

U.S. PATENT DOCUMENTS 5,682,886 A * 11/1997 Delp .................... A61B 17/154
                                                          128/920
2011/0029093 A1* 2/2011 Bojarski ............. A61F 2/30942
                                                         623/20.35

* cited by examiner

*Primary Examiner* — Ann Schillinger
(74) *Attorney, Agent, or Firm* — Fish & Richardson P.C.

(57) ABSTRACT

The present application discloses a method of producing a knee replacement implant, an implant for knee replacement formed by using the method, and a knee replacement implant. The method includes: defining a hip center, a knee center, an ankle center and a posterior femoral condylar axis of a lower limb; generating femoral geometric parameters and tibial geometric parameters, the femoral geometric parameters and the tibial geometric parameters being measured in relation to the hip center, the knee center, the ankle center and the posterior femoral condylar axis; collecting anthropometric data from a defined population using the femoral geometric parameters and the tibial geometric parameters; and creating a femoral component and/or a tibial component using the collected anthropometric data.

16 Claims, 17 Drawing Sheets

(51) Int. Cl.
*A61B 17/16* (2006.01)
*A61F 2/30* (2006.01)
(52) U.S. Cl.
CPC .............. *A61F 2002/30945* (2013.01); *A61F 2002/30952* (2013.01)
(58) Field of Classification Search
CPC .......... A61B 17/1764; A61B 2034/108; A61B 17/1703; A61B 17/1675; A61B 5/4585; A61B 2034/101; A61B 2034/102; A61B 2090/374; A61B 5/1121
See application file for complete search history.

S1100

```
marking a surface area from an inter-notch      S1110
arc to an end of a posterior femur condyle
   of a femur condyle of the lower limb
```

```
fitting a cylinder with the marked surface area  S1120
```

```
defining an axis of the fitted cylinder as      S1130
    the posterior femoral condylar axis
```

FIG. 2

S1200 building a plurality of coordinate systems based on the hip center, knee center, ankle center and posterior femoral condylar axis of the lower limb — S1210 defining the femoral geometric parameters and the tibial geometric parameters by using the built coordinate systems — S1220

```
┌─────────────────────────────────────────┐
│  locating a lower-limb mechanical axis  │
│  of the lower limb, the lower-limb      │──S1211
│  mechanical axis being through the hip  │
│  center and the ankle center            │
└─────────────────────────────────────────┘
                     │
┌─────────────────────────────────────────┐
│  creating a lower-limb coronal plane,   │
│  the lower-limb coronal plane being     │──S1212
│  through the lower-limb mechanical axis │
│  and parallel to the posterior femoral  │
│  condylar axis                          │
└─────────────────────────────────────────┘
                     │
┌─────────────────────────────────────────┐
│  positioning an origin of the lower-    │──S1213
│  limb coordinate system at the hip      │
│  center                                 │
└─────────────────────────────────────────┘
                     │
┌─────────────────────────────────────────┐
│  setting a Y-axis direction of the      │
│  lower-limb coordinate system from the  │──S1214
│  ankle center to the hip center         │
└─────────────────────────────────────────┘
                     │
┌─────────────────────────────────────────┐
│  setting a Z-axis direction of the      │
│  lower-limb coordinate system, the Z-   │
│  axis direction being perpendicular to  │──S1215
│  the lower-limb coronal plane and       │
│  extending from a rear to a front of    │
│  the lower limb                         │
└─────────────────────────────────────────┘
                     │
┌─────────────────────────────────────────┐
│  setting an X-axis direction of the     │──S1216
│  lower-limb coordinate system according │
│  to a right hand rule                   │
└─────────────────────────────────────────┘
```

```
creating a femur condyle coronal plane through     S1211"
the posterior femoral condylar axis and the hip
               joint center positioning an origin of the femur condyle        S1212"
    coordinate system at the knee center setting a Y-axis direction of the femur condyle   S1213"
    coordinate system, the Y-axis direction being
    perpendicular to the posterior femoral condylar setting a Z-axis direction of the femur condyle   S1214"
coordinate system, the Z-axis direction being
perpendicular to the femur condyle coronal plane and
extending from a rear to a front of the lower limb setting an X-axis direction of the femur condyle  S1215"
    coordinate system according to a right hand rule
```

```
┌─────────────────────────────────────────────┐
│  creating a tibia coronal plane, the tibia  │──S1211'''
│  coronal plane being through the posterior  │
│  femoral condylar axis and the ankle center │
└─────────────────────────────────────────────┘
                      │
┌─────────────────────────────────────────────┐
│    positioning an origin of the tibia       │──S1212'''
│    coordinate system at the knee center     │
└─────────────────────────────────────────────┘
                      │
┌─────────────────────────────────────────────┐
│  setting a Y-axis direction of the tibia coordinate │──S1213'''
│  system from the ankle center to the knee center    │
└─────────────────────────────────────────────┘
                      │
┌─────────────────────────────────────────────┐
│  setting a Z-axis direction of the tibia coordinate │──S1214'''
│  system, the Z-axis direction being perpendicular to│
│  the tibia coronal plane and extending from a rear to│
│  a front of the lower limb                          │
└─────────────────────────────────────────────┘
                      │
┌─────────────────────────────────────────────┐
│   setting an X-axis direction of the tibia  │──S1215'''
│  coordinate system according to a right hand rule │
└─────────────────────────────────────────────┘
```

FIG. 14

METHOD FOR PRODUCING KNEE REPLACEMENT IMPLANT AND IMPLANT FOR KNEE REPLACEMENT

TECHNICAL FIELD

The present application relates to a method for producing a knee replacement implant as well as a knee replacement implant formed by using the method.

BACKGROUND

Total knee replacement surgery is a common orthopaedic surgery for patients suffering from their severely damaged limb by arthritis or injury. During the surgery, fractures or damaged fragments are fixed internally by suitable implants or replaced by best fit available prosthesis.

The implants and prostheses available in the prior art are designed according to few races. However, extensive studies have indicated that anatomies of human are different across different races. Due to the inadequacy of available sizes of implants and prostheses and the lack of incorporation of anthropometric characteristics of knee data of many races into the design of implants and prostheses, a number of patients of the races are reported to be un-matched with available implants and prostheses. Undersize of the implant and prosthesis will lead to subsidence of the implant and prosthesis, while the overhang of the component will result in soft tissue abrasion and ultimate operation failure.

SUMMARY

According to an aspect of the present application, a method of producing a knee replacement implant is provided. The method includes: defining a hip center, a knee center, an ankle center and a posterior femoral condylar axis of a lower limb; generating femoral geometric parameters and tibial geometric parameters, the femoral geometric parameters and the tibial geometric parameters being measured in relation to the hip center, the knee center, the ankle center and the posterior femoral condylar axis; collecting anthropometric data from a defined population using the femoral geometric parameters and the tibial geometric parameters; and creating a femoral component and/or a tibial component using the collected anthropometric data.

According to another aspect of the present application, a knee replacement implant including a femoral component having femoral geometric parameters and/or a tibial component having tibial geometric parameters is provided. The femoral geometric parameters may be measured in relation to a hip center, a knee center, an ankle center and a posterior femoral condylar axis of a lower limb; and the tibial geometric parameters may be measured in relation to the hip center, the knee center, the ankle center and the posterior femoral condylar axis. The femoral geometric parameters and the tibial geometric parameters may be used to collect anthropometric data, from a defined population, for creating the femoral component and the tibial component.

According to a further aspect of the present application, an implant for knee replacement is provided, which may be formed by using the above method.

According to embodiments of the present application, a femoral component and/or a tibial component of a knee replacement implant suitable for a certain population may be created by using the collected anthropometric data from the population. The collected anthropometric data from a certain population may be measured and further analyzed for reproducing the shape of population anatomies in implants and prostheses.

BRIEF DESCRIPTION OF THE DRAWINGS

FIG. 2 is a flowchart illustrating the defining of the posterior femoral condylar axis according to an embodiment of the present application;

FIG. 7 is a flowchart illustrating the generating of the femoral geometric parameters and the tibial geometric parameters according to an embodiment of the present application;

FIG. 8 is a flowchart illustrating the building of the lower-limb coordinate system according to an embodiment of the present application;

FIG. 12 is a flowchart illustrating the building of the femur condyle coordinate system according to an embodiment of the present application;

FIG. 14 is a flowchart illustrating the building of the tibia coordinate system according to an embodiment of the present application;

DETAILED DESCRIPTION OF EMBODIMENTS

Hereinafter, a detailed description of the present application will be given with reference to the appended drawings.

The knee replacement implants described herein may include implants and prostheses used for knee replacement. The implants may used for fixing fractures or damaged fragments internally. The prostheses may used for replacing the whole or a part of a bone.

Figure 1:
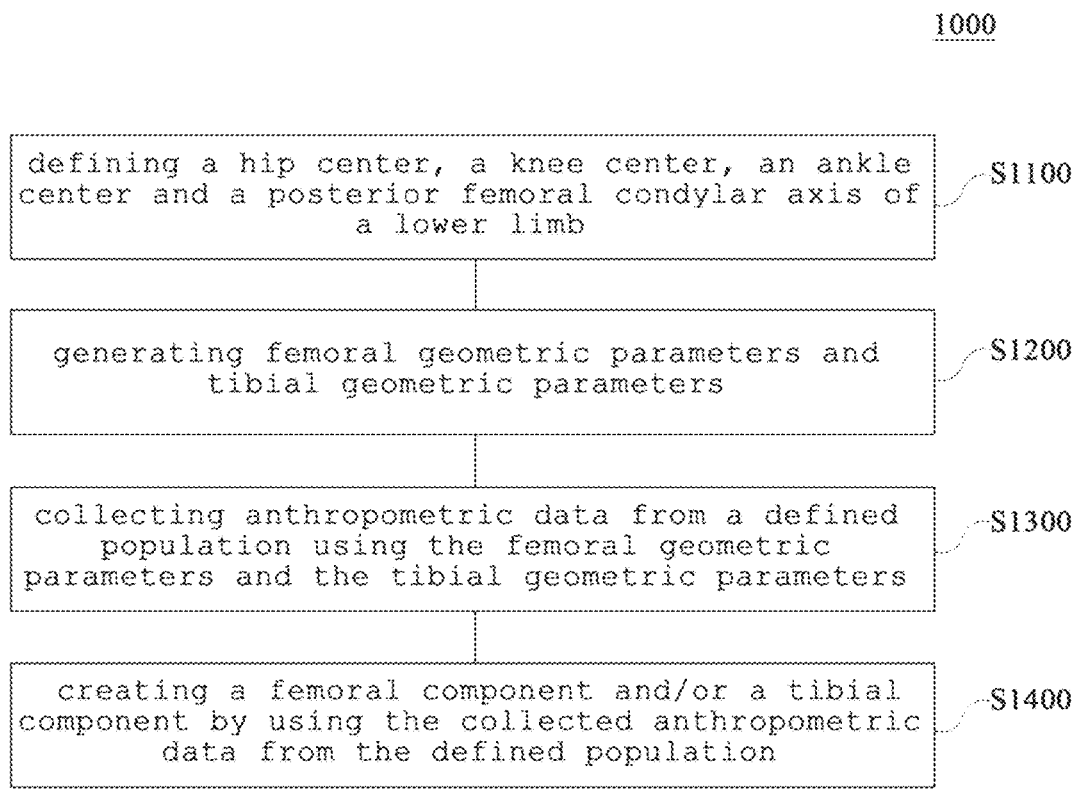
FIG. 1 is a flowchart illustrating a method of producing a knee replacement implant according to an embodiment of the present application.

FIG. 1 is a flowchart illustrating a method of producing a knee replacement implant according to an embodiment of the present application. As shown in FIG. 1, the method 1000 includes steps S1100-S1400.

At step S1100, a hip center, a knee center, an ankle center and a posterior femoral condylar axis of a lower limb are defined. In the embodiment, the hip center, knee center, ankle center and posterior femoral condylar axis of a lower limb may be defined in a medical image processing software, such as Mimics having a geometry fitting function on corresponding anatomical landmarks. A detailed discussion of the hip center, knee center, ankle center and posterior femoral condylar axis will be given later.

At step S1200, femoral geometric parameters and tibial geometric parameters are generated. Specifically, the femoral geometric parameters and the tibial geometric parameters are measured in relation to the hip center, the knee center, the ankle center and the posterior femoral condylar axis. In the embodiment, the femoral geometric parameters and tibial geometric parameters may be generated in a computer aided drawing software, such as Solidworks. A detailed discussion of generating the femoral geometric parameters and tibial geometric parameters will be given later.

At step S1300, anthropometric data is collected from a defined population using the femoral geometric parameters and the tibial geometric parameters. In this step S1300, the anthropometric data may be collected from a specified population so that the knee replacement implant to be produced may suitable for a person of the population. In the embodiment, the anthropometric data may be collected by using the CAD drawing tools.

At step S1400, a femoral component and/or a tibial component are created by using the collected anthropometric data from the defined population.

As such, a femoral component and/or a tibial component of a knee replacement implant suitable for a certain population may be created by using the collected anthropometric data from the population. The collected anthropometric data from a certain population may be measured and further analyzed for reproducing the shape of population anatomies in implants and prostheses. For industry manufacture, the anthropometric data of a plurality of samples from a certain population may be used for designing the knee replacement implants suitable for the certain population. For a patient's surgery, his own anthropometric data or the anthropometric data of one or more persons from the patient's population may be used for designing a knee replacement implant suitable for the patient.

FIG. 2 is a flowchart illustrating the defining of the posterior femoral condylar axis according to an embodiment of the present application. As shown in FIG. 2, step S1100 includes sub-steps S1110-S1130.

At sub-step S1110, a surface area from an inter-notch arc to an end of a posterior femur condyle of a femur condyle of the lower limb is marked. At sub-step S1120, a cylinder is fitted with the marked surface area. At sub-step S1130, an axis of the fitted cylinder is defined as the posterior femoral condylar axis.

As mentioned above, step S1100 may be implemented in a medical image processing software, such as Mimics having a geometry fitting function on corresponding anatomical landmarks. That is, sub-steps S1110-S1130 may be implemented in the medical image processing software.

Figure 3:
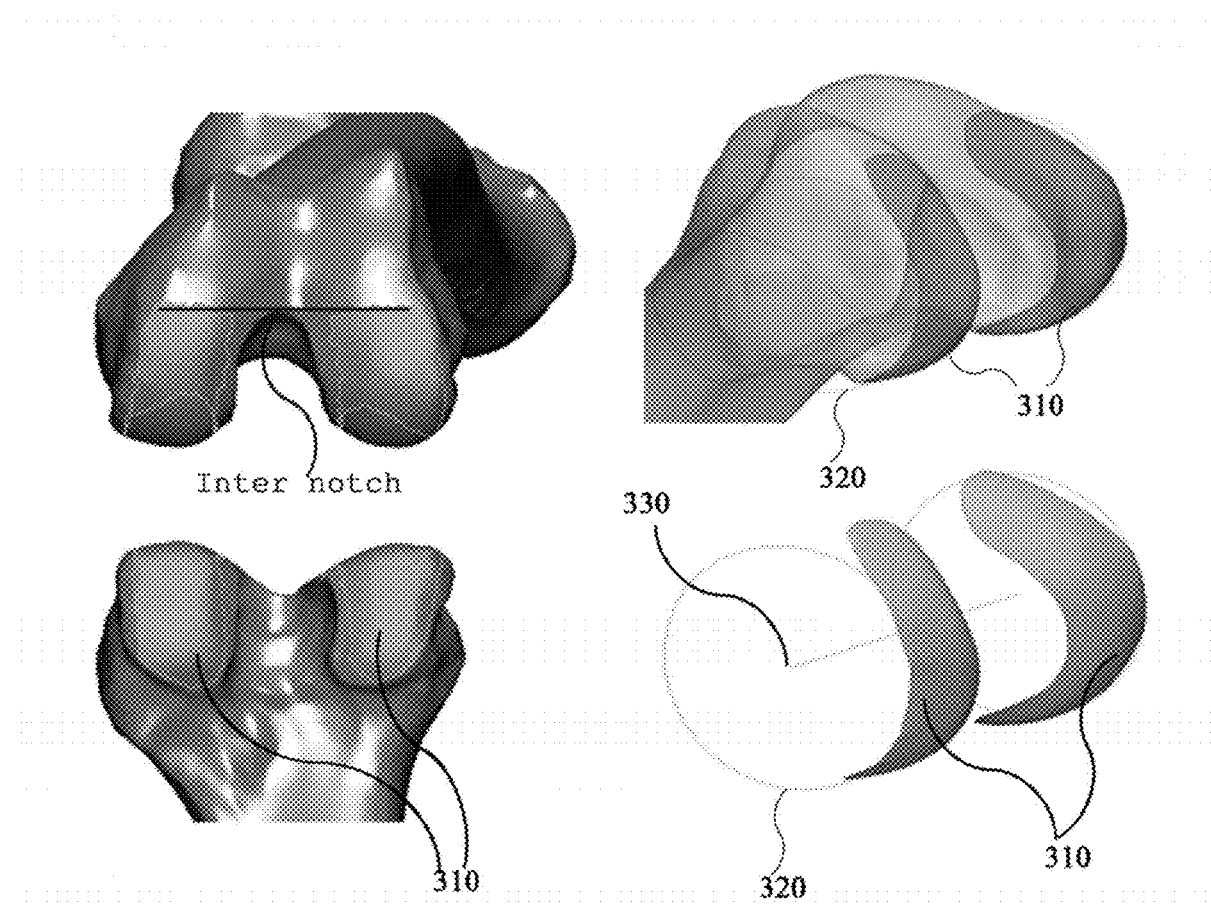
FIG. 3 shows a diagram of a posterior femoral condyle viewed from three different directions, in which the posterior femoral condylar axis is defined according to an embodiment of the present application.

FIG. 3 shows a diagram of a posterior femoral condyle viewed from three different directions, in which the posterior femoral condylar axis is defined according to an embodiment of the present application. As shown in FIG. 3, a surface area 310 from the inter-notch arc to the end of the posterior femur condyle of the femur condyle is marked, a cylinder 320 is fitted with the marked surface area 310, and then an axis 330 of the fitted cylinder 320 is defined as the posterior femoral condylar axis.

Figure 4:
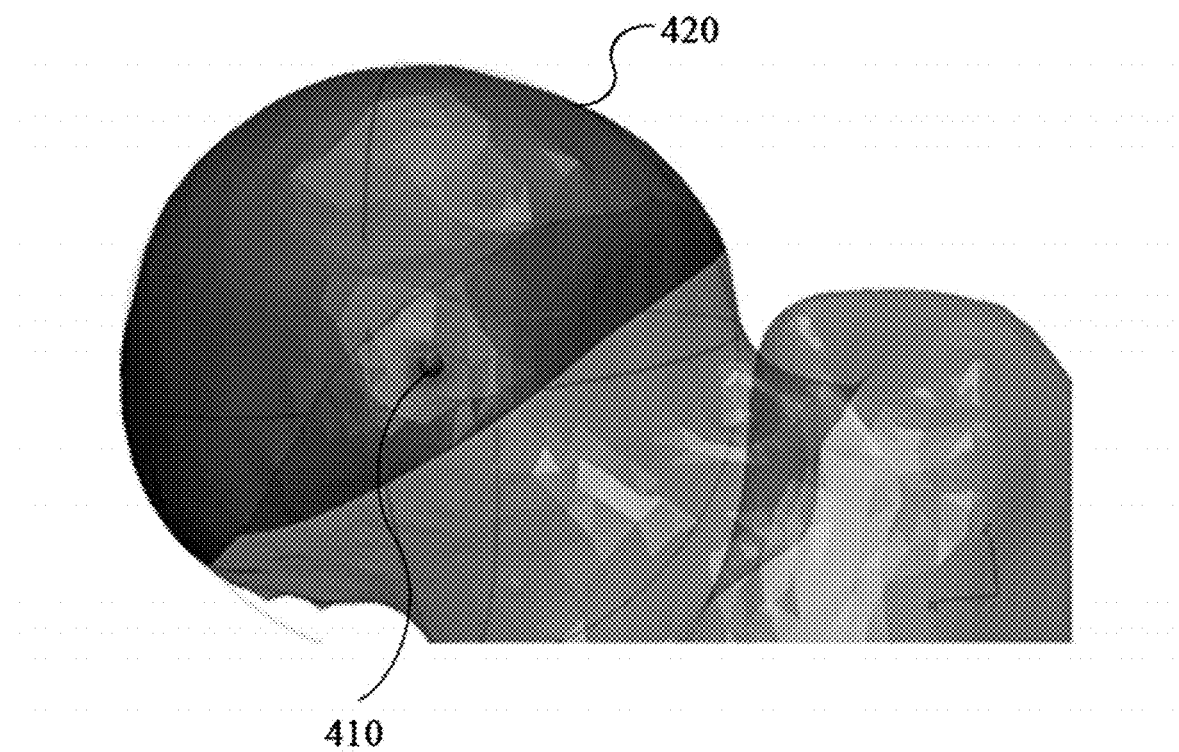
FIG. 4 shows a diagram of a femur head in which the hip center is defined according to an embodiment of the present application.

FIG. 4 shows a diagram of a femur head in which the hip center is defined according to an embodiment of the present application. As shown in FIG. 4, the hip center 410 is the center of the sphere fitted with the femur head surface 420 of the lower limb.

Figure 5:
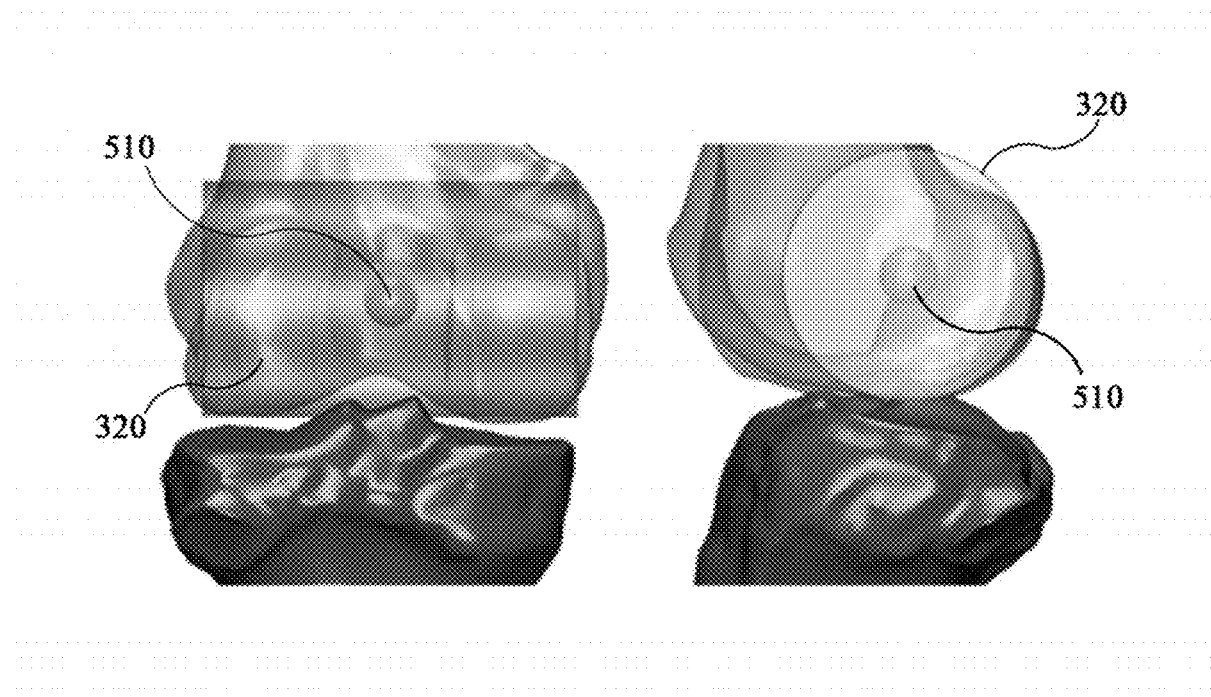
FIG. 5 shows a diagram of a knee joint viewed from two different directions, in which the knee center is defined according to an embodiment of the present application.

FIG. 5 shows a diagram of a knee joint viewed from two different directions, in which the knee center is defined according to an embodiment of the present application. As shown in FIG. 5, the knee center 510 is the center of the axis of the fitted cylinder 320 as described with reference to FIG. 3.

Figure 6:
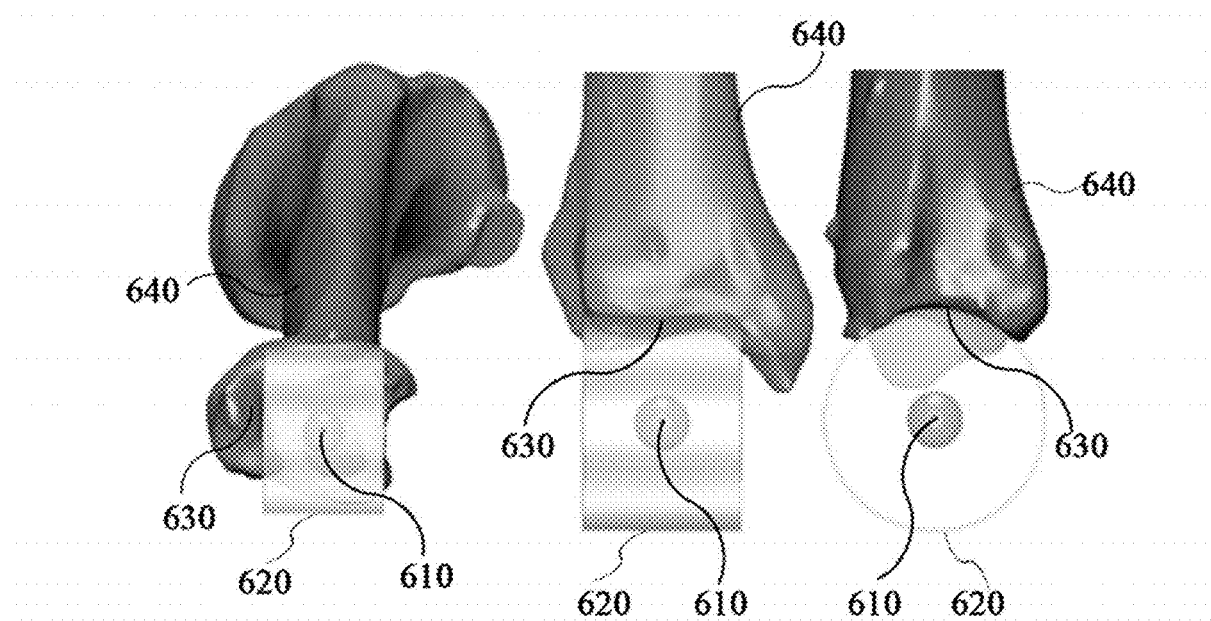
FIG. 6 shows a diagram of a distal tibia viewed from three different directions, in which the ankle center is defined according to an embodiment of the present application.

FIG. 6 shows a diagram of a part of a distal tibia viewed from three different directions, in which the ankle center is defined according to an embodiment of the present application. As shown in FIG. 6, the ankle center 610 is a gravity center of a cylinder 620 fitted with an articular surface 630 of the distal tibia 640.

As discussed above, the hip center, knee center, ankle center and posterior femoral condylar axis of the lower limb are defined so that the femoral geometric parameters and the tibial geometric parameters may be measured in relation to the defined hip center, knee center, ankle center and posterior femoral condylar axis, which is a unique design for collecting anthropometric data.

FIG. 7 is a flowchart illustrating the generating of the femoral geometric parameters and the tibial geometric parameters according to an embodiment of the present application. As shown in FIG. 7, step S1200 includes sub-steps S1210-S1220.

At sub-step S1210, a plurality of coordinate systems is built based on the hip center, knee center, ankle center and posterior femoral condylar axis of the lower limb. Then, at sub-step S1220, the femoral geometric parameters and the tibial geometric parameters are defined by using the built coordinate systems. A detailed discussion of the coordinate systems will be given later.

As mentioned above, step S1200 may be implemented in a computer aided drawing software, such as Solidworks. That is, the plurality of coordinate systems may be built and the femoral geometric parameters and the tibial geometric parameters may be defined, in the computer aided drawing software.

According to an embodiment of the present application, the plurality of coordinate systems includes a lower-limb coordinate system. FIG. 8 is a flowchart illustrating the building of the lower-limb coordinate system according to an embodiment of the present application. As shown in FIG. 8, sub-step S1210 includes sub-steps S1211-S1216.

At sub-step S1211, a lower-limb mechanical axis of the lower limb is located to be through the hip center and the ankle center. At sub-step S1212, a lower-limb coronal plane is created to be through the lower-limb mechanical axis and parallel to the posterior femoral condylar axis. At sub-step S1213, the origin of the lower-limb coordinate system is positioned at the hip center. At sub-step S1214, the Y-axis direction of the lower-limb coordinate system is set to be from the ankle center to the hip center. At sub-step S1215, the Z-axis direction of the lower-limb coordinate system is set to be perpendicular to the lower-limb coronal plane and extend from the rear to the front of the lower limb. At sub-step S1216, the X-axis direction of the lower-limb coordinate system is set according to the right hand rule.

Figure 9:
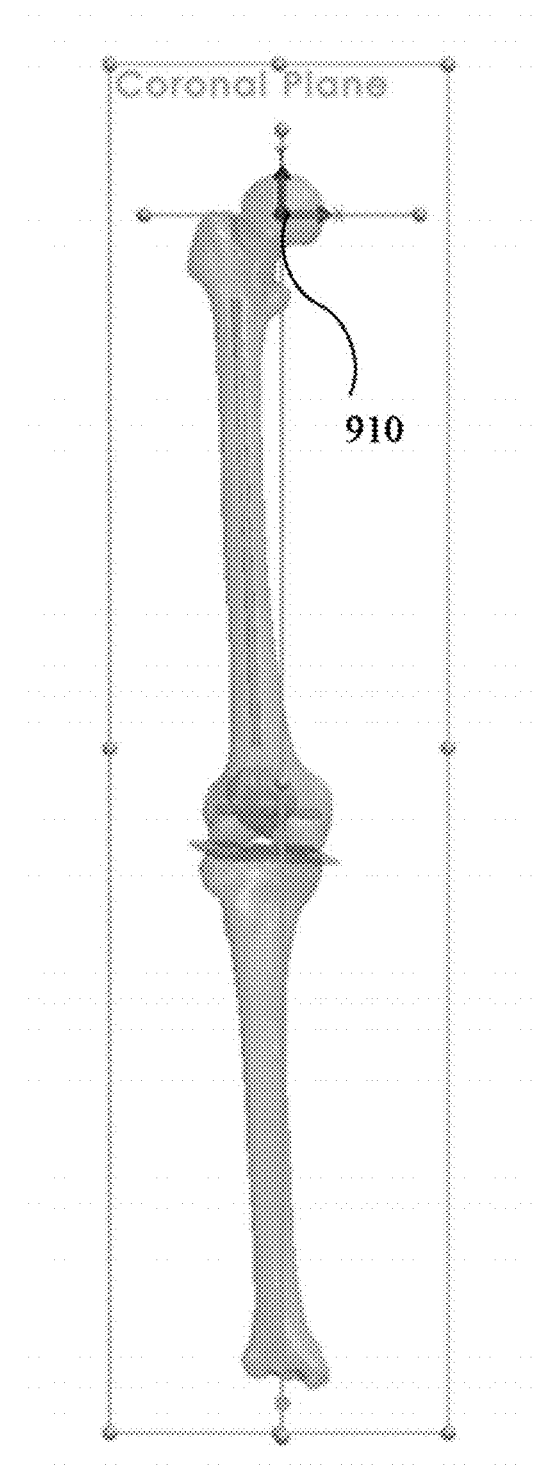
FIG. 9 shows a built lower-limb coordinate system according to an embodiment of the present application.

As such, the lower-limb coordinate system is built. FIG. 9 shows a built lower-limb coordinate system according to an embodiment of the present application, in which the origin 910 as well as the X axis, Y axis and Z axis of the lower-limb coordinate system are positioned according to the process shown in FIG. 8.

Figure 10:
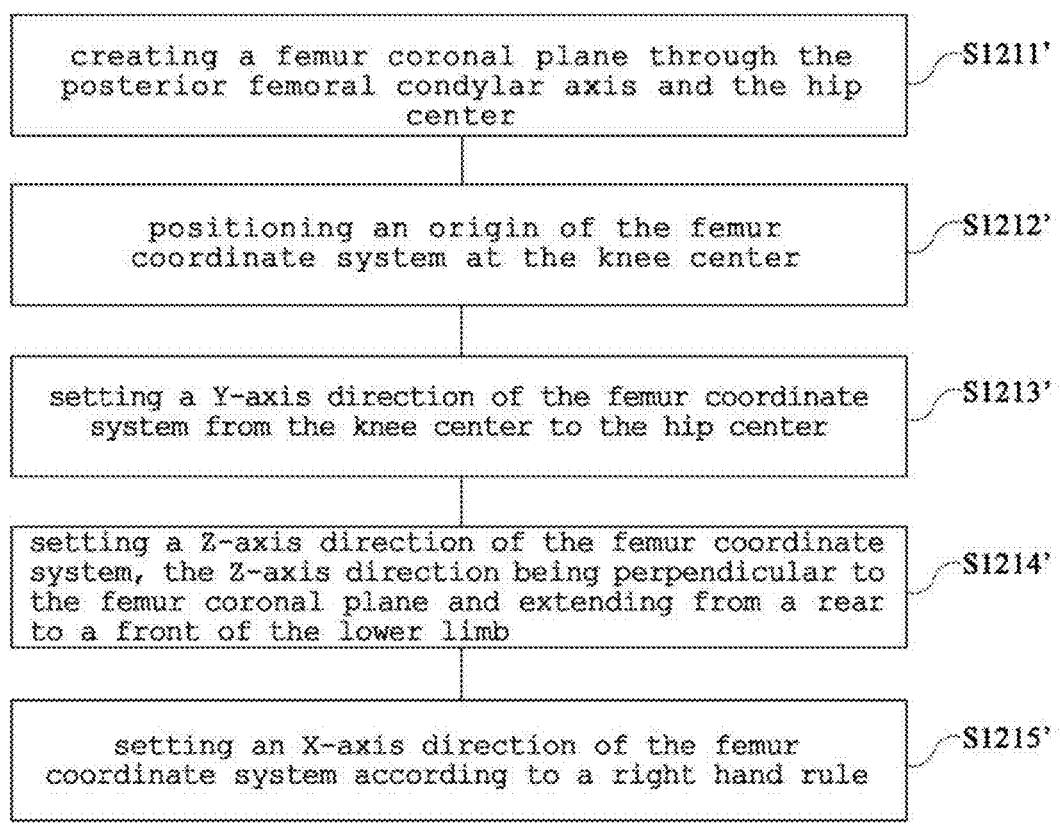
FIG. 10 is a flowchart illustrating the building of the femur coordinate system according to an embodiment of the present application.

According to an embodiment of the present application, the plurality of coordinate systems includes a femur coordinate system. FIG. 10 is a flowchart illustrating the building of the femur coordinate system according to an embodiment of the present application. As shown in FIG. 10, sub-step S1210 includes sub-steps S1211'-S1215'.

At sub-step S1211', a femur coronal plane is created to be through the posterior femoral condylar axis and the hip center. At sub-step S1212', an origin of the femur coordinate system is positioned at the knee center. At sub-step S1213', the Y-axis direction of the femur coordinate system is set to be from the knee center to the hip center. At sub-step S1214', the Z-axis direction of the femur coordinate system is set to be perpendicular to the femur coronal plane and extend from the rear to the front of the lower limb. At sub-step S1215', the X-axis direction of the femur coordinate system is set according to the right hand rule.

Figure 11:
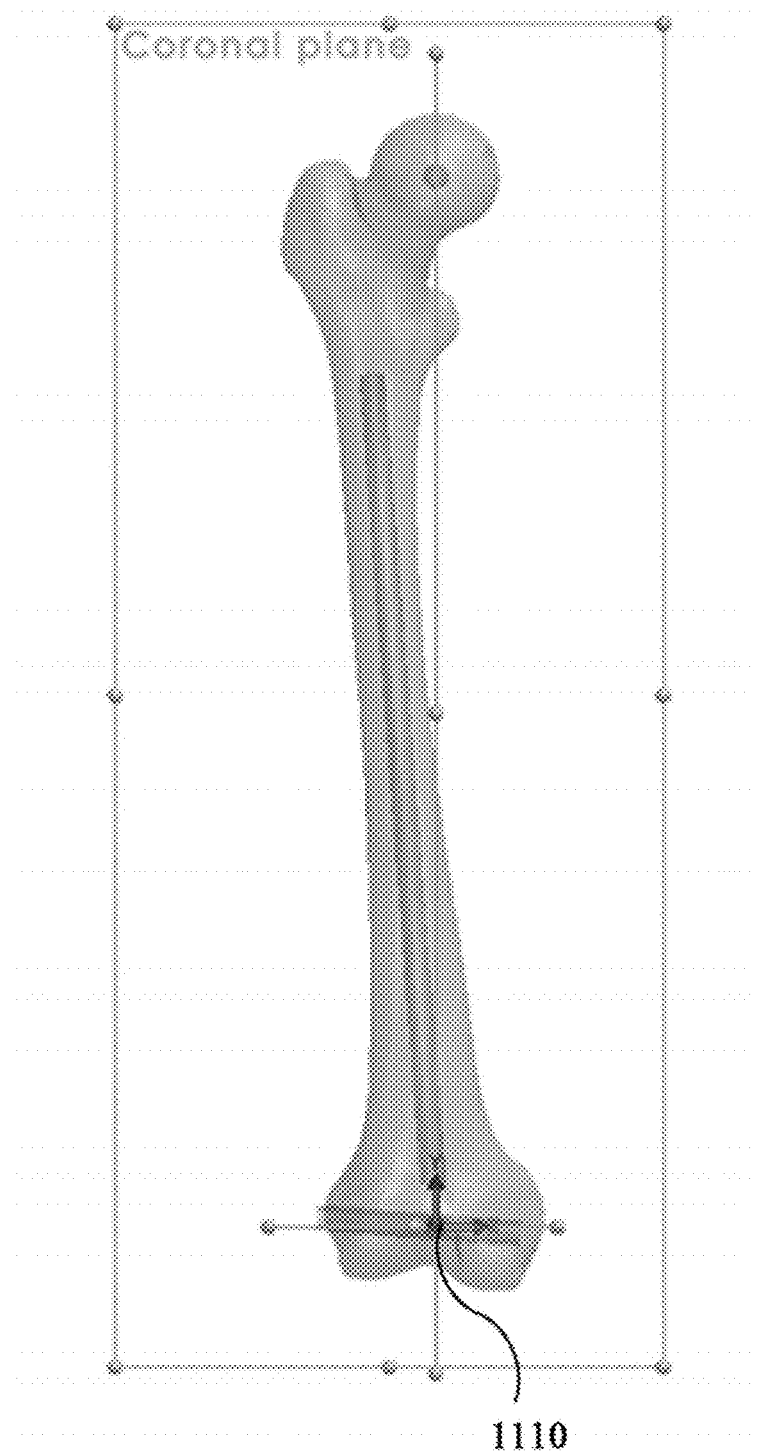
FIG. 11 shows a built femur coordinate system according to an embodiment of the present application.

As such, the femur coordinate system is built. FIG. 11 shows a built femur coordinate system according to an embodiment of the present application, in which the origin 1110 as well as the X axis, Y axis and Z axis of the femur coordinate system are positioned according to the process shown in FIG. 10.

According to an embodiment of the present application, the plurality of coordinate systems includes a femur condyle coordinate system. FIG. 12 is a flowchart illustrating the building of the femur condyle coordinate system according to an embodiment of the present application. As shown in FIG. 12, sub-step S1210 includes sub-steps S1211"-S1215".

At sub-step S1211", a femur condyle coronal plane is created to be through the posterior femoral condylar axis and the hip joint center. At sub-step S1212", an origin of the femur condyle coordinate system is positioned at the knee center. At sub-step S1213", the Y-axis direction of the femur condyle coordinate system is set to be perpendicular to the posterior femoral condylar. At sub-step S1214", the Z-axis direction of the femur condyle coordinate system is set to be perpendicular to the femur condyle coronal plane and extend from the rear to the front of the lower limb. At sub-step S1215", the X-axis direction of the femur condyle coordinate system is set according to the right hand rule.

Figure 13:
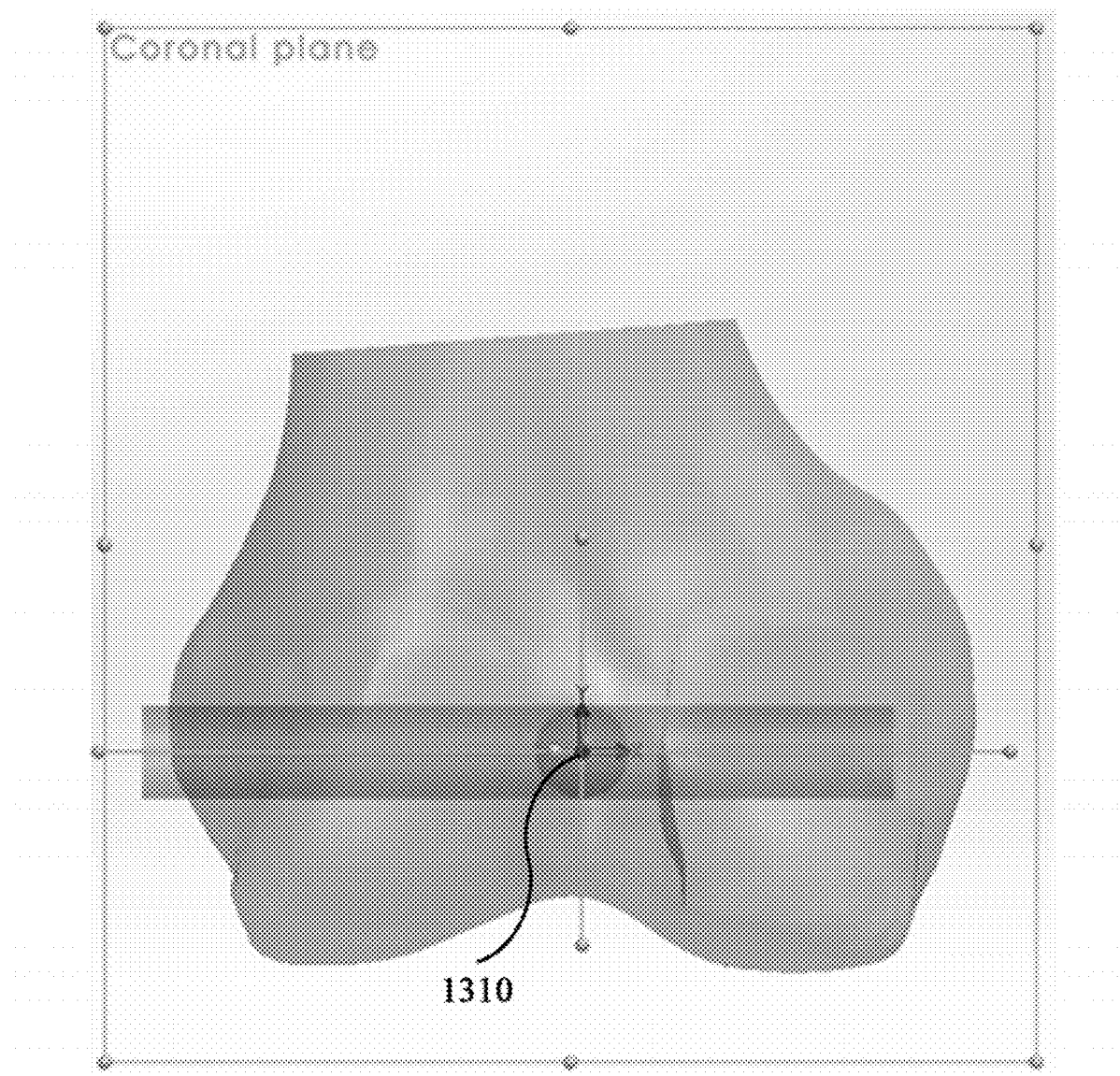
FIG. 13 shows a built femur condyle coordinate system according to an embodiment of the present application.

As such, the femur condyle coordinate system is built. FIG. 13 shows a built femur condyle coordinate system according to an embodiment of the present application, in which the origin 1310 as well as the X axis, Y axis and Z axis of the femur condyle coordinate system are positioned according to the process shown in FIG. 12.

According to an embodiment of the present application, the plurality of coordinate systems includes a tibia coordinate system. FIG. 14 is a flowchart illustrating the building of the tibia coordinate system according to an embodiment of the present application. As shown in FIG. 14, sub-step S1210 includes sub-steps S1211'''-S1215'''.

At sub-step S1211''', a tibia coronal plane is created to be through the posterior femoral condylar axis and the ankle center. At sub-step S1212''', an origin of the tibia coordinate system is positioned at the knee center. At sub-step S1213''', the Y-axis direction of the tibia coordinate system is set from the ankle center to the knee center. At sub-step S1214''', the Z-axis direction of the tibia coordinate system is set to be perpendicular to the tibia coronal plane and extend from the rear to the front of the lower limb. At sub-step S1215''', the X-axis direction of the tibia coordinate system is set according to the right hand rule.

Figure 15:
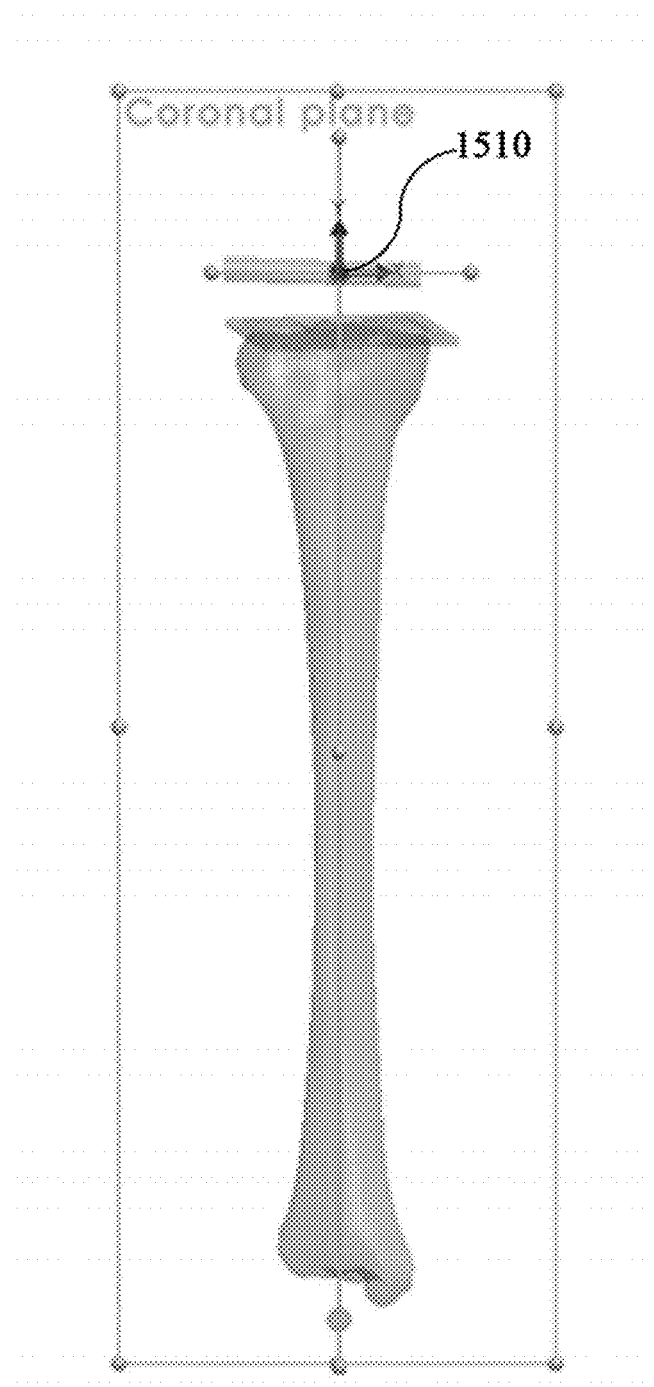
FIG. 15 shows a built tibia coordinate system according to an embodiment of the present application.

As such, the tibia coordinate system is built. FIG. 15 shows a built tibia coordinate system according to an embodiment of the present application, in which the origin 1510 as well as the X axis, Y axis and Z axis of the tibia coordinate system are positioned according to the process shown in FIG. 14.

From the above, the lower-limb coordinate system, femur coordinate system, femur condyle coordinate system, and tibia coordinate system are designed and built for collecting anthropometric data. According to an embodiment of the present application, at step S1300 of collecting the anthropometric data, the anthropometric data of a femur, a femur condyle, a tibia and a tibial plateau of the lower limb can be measured by using the plurality of coordinate systems. In an example, the collected anthropometric data may include coordinates and curvatures defined by the plurality of coordinate systems.

As mentioned above, step S1300 may be implemented by using the CAD drawing tools. That is, the anthropometric data of a femur, a femur condyle, a tibia and a tibial plateau of the lower limb may be measured by using the CAD drawing tools.

Figure 16:
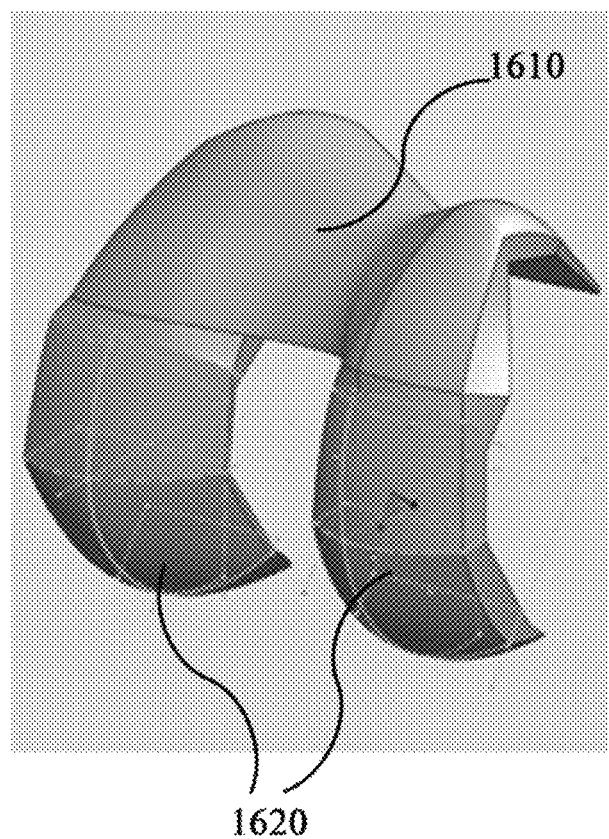
FIG. 16 shows a simulated distal femur according to an embodiment of the present application.

FIG. 16 shows a simulated distal femur according to an embodiment of the present application. In the embodiment, at step S1400, the creating of the femoral component may include simulating a distal femur based on the collected anthropometric data. As shown in FIG. 16, the distal femur 1600 may be simulated by: simulating a patella groove 1610 and a posterior femoral condyle 1620 based on the collected anthropometric data, and combining the simulated patella groove 1610 and posterior femoral condyle 1620.

Alternatively, the simulated patella groove 1610 may be constructed by forming a radial section curve and a sagittal section curve of the patella groove 1610, and the simulated posterior femoral condyle 1620 may be constructed by forming a radial section curve and a sagittal section curve of the posterior femoral condyle 1620.

Figure 17:
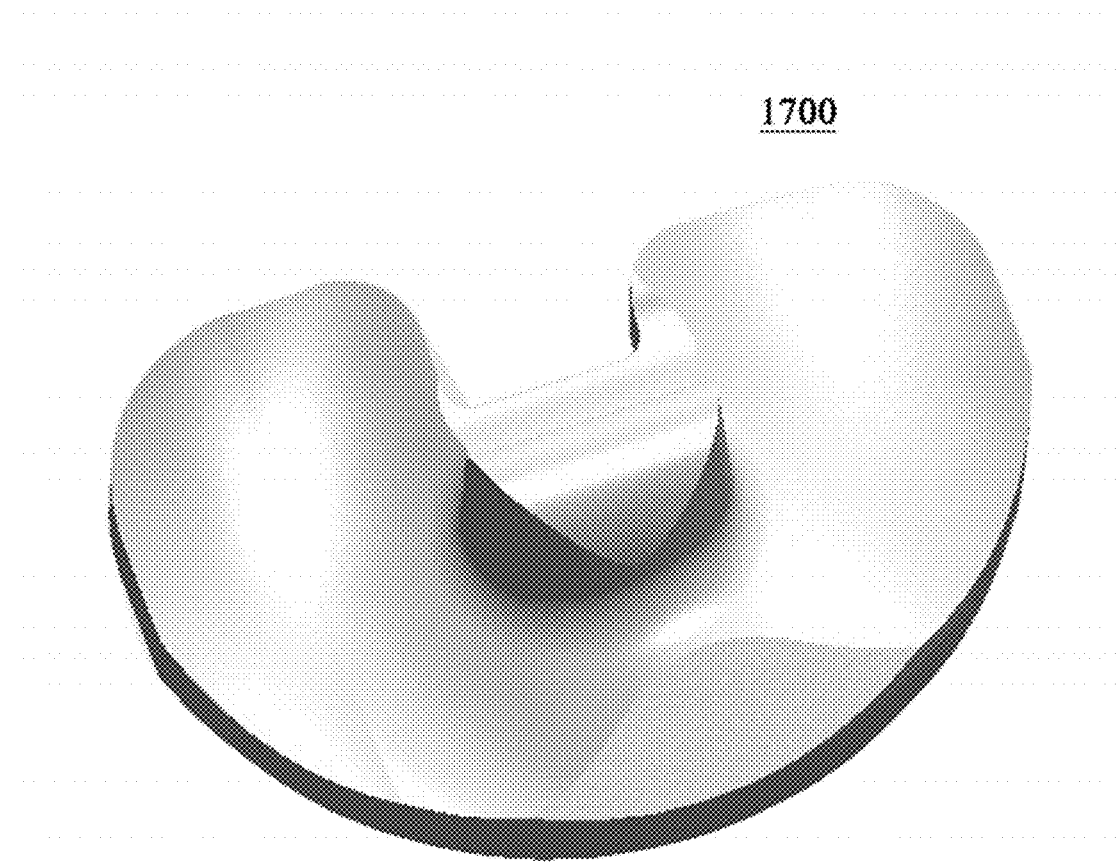
FIG. 17 shows a simulated tibial plateau according to an embodiment of the present application.

FIG. 17 shows a simulated tibial plateau according to an embodiment of the present application. In the embodiment, at step S1400, the creating of the tibial component may include simulating a proximal tibia based on the collected anthropometric data. As shown in FIG. 17, the proximal tibia is simulated by simulating the tibial plateau 1700 based on the collected anthropometric data.

Alternatively, the simulated tibial plateau 1700 may be constructed by forming a coronal section curve, a sagittal section curve, and an axial circumference of the tibial plateau 1700.

In another aspect, the present application provides a knee replacement implant including a femoral component having femoral geometric parameters and/or a tibial component having tibial geometric parameters. The femoral geometric parameters may be measured in relation to a hip center, a knee center, an ankle center and a posterior femoral condylar axis of a lower limb; and the tibial geometric parameters may be measured in relation to the hip center, the knee center, the ankle center and the posterior femoral condylar axis. The femoral geometric parameters and the tibial geometric parameters may be used to collect anthropometric data, from a defined population, for creating the femoral component and the tibial component.

In a further aspect, the present application provides an implant for knee replacement, which may be formed by using the method as described above.

Although the above descriptions include many specific arrangements and parameters, it should be noted that these specific arrangements and parameters only served to illustrate one embodiment of the present application. This should not be considered as the limitations on the scope of the application. It can be understood by those skilled in the art that various modifications, additions and substitutions may be made thereto without departing from the scope and spirit of the present application. Therefore, the scope of the present application should be construed on the basis of the appended claims.

What is claimed is:

1. A method of producing a knee replacement implant, the method comprising:
    defining a hip center, a knee center, an ankle center and a posterior femoral condylar axis of a lower limb;
    generating femoral geometric parameters and tibial geometric parameters, the femoral geometric parameters and the tibial geometric parameters being measured in relation to the hip center, the knee center, the ankle center and the posterior femoral condylar axis;
    collecting anthropometric data from a defined population using the femoral geometric parameters and the tibial geometric parameters; and
    creating a femoral component and/or a tibial component using the collected anthropometric data,
    wherein the generating of the femoral geometric parameters and the tibial geometric parameters comprises:
        building a plurality of different coordinate systems based on the hip center, the knee center, the ankle center and the posterior femoral condylar axis; and
        defining the femoral geometric parameters and the tibial geometric parameters by using the different coordinate systems, respectively; and
    wherein the defining of the posterior femoral condylar axis comprises:
        marking a surface area from an inter-notch arc to an end of a posterior femur condyle of a femur condyle of the lower limb;
        fitting a cylinder with the marked surface area, in which the cylinder extends along a direction from a medial femoral condyle to a lateral femoral condyle; and
        defining an axis of the fitted cylinder as the posterior femoral condylar axis.

2. The method of claim 1, wherein the hip center is a center of a sphere fitted with a femur head surface of the lower limb.

3. The method of claim 1, wherein the knee center is a center of the axis of the fitted cylinder.

4. The method of claim 1, wherein the ankle center is a gravity center of a cylinder fitted with an articular surface of a distal tibia of the lower limb.

5. The method of claim 1, wherein the plurality of coordinate systems comprises a lower-limb coordinate system, and the building of the plurality of coordinate systems comprises:
    locating a lower-limb mechanical axis of the lower limb, the lower-limb mechanical axis being through the hip center and the ankle center;
    creating a lower-limb coronal plane, the lower-limb coronal plane being through the lower-limb mechanical axis and parallel to the posterior femoral condylar axis;
    positioning an origin of the lower-limb coordinate system at the hip center;
    setting a Y-axis direction of the lower-limb coordinate system from the ankle center to the hip center;
    setting a Z-axis direction of the lower-limb coordinate system, the Z-axis direction being perpendicular to the lower-limb coronal plane and extending from a rear to a front of the lower limb; and
    setting an X-axis direction of the lower-limb coordinate system according to a right hand rule.

6. The method of claim 1, wherein the plurality of coordinate systems comprises a femur coordinate system, and the building of the plurality of coordinate systems comprises:
    creating a femur coronal plane through the posterior femoral condylar axis and the hip center;
    positioning an origin of the femur coordinate system at the knee center;
    setting a Y-axis direction of the femur coordinate system from the knee center to the hip center;
    setting a Z-axis direction of the femur coordinate system, the Z-axis direction being perpendicular to the femur coronal plane and extending from a rear to a front of the lower limb; and
    setting an X-axis direction of the femur coordinate system according to a right hand rule.

7. The method of claim 1, wherein the plurality of coordinate systems comprises a femur condyle coordinate system, and the building of the plurality of coordinate systems comprises:
    creating a femur condyle coronal plane through the posterior femoral condylar axis and the hip joint center;
    positioning an origin of the femur condyle coordinate system at the knee center;
    setting a Y-axis direction of the femur condyle coordinate system, the Y-axis direction being perpendicular to the posterior femoral condylar;
    setting a Z-axis direction of the femur condyle coordinate system, the Z-axis direction being perpendicular to the femur condyle coronal plane and extending from a rear to a front of the lower limb; and
    setting an X-axis direction of the femur condyle coordinate system according to a right hand rule.

8. The method of claim 1, wherein the plurality of coordinate systems comprises a tibia coordinate system, and the building of the plurality of coordinate systems comprises:
    creating a tibia coronal plane, the tibia coronal plane being through the posterior femoral condylar axis and the ankle center;
    positioning an origin of the tibia coordinate system at the knee center;
    setting a Y-axis direction of the tibia coordinate system from the ankle center to the knee center;
    setting a Z-axis direction of the tibia coordinate system, the Z-axis direction being perpendicular to the tibia coronal plane and extending from a rear to a front of the lower limb; and
    setting an X-axis direction of the tibia coordinate system according to a right hand rule.

9. The method of claim 1, wherein the collecting of the anthropometric data comprises measuring anthropometric data of a femur, a femur condyle, a tibia and a tibial plateau of the lower limb using the plurality of coordinate systems.

10. The method of claim 1, wherein the collected anthropometric data comprises coordinates and curvatures defined by the plurality of coordinate systems.

11. The method of claim 1, wherein the creating of the femoral component comprises:
    simulating a distal femur based on the collected anthropometric data, wherein the distal femur is simulated by: simulating a patella groove and a posterior femoral condyle based on the collected anthropometric data, and combining the simulated patella groove and posterior femoral condyle.

12. The method of claim 11, wherein the simulated patella groove is constructed by forming a radial section curve and a sagittal section curve of the patella groove.

13. The method of claim 11, wherein the simulated posterior femoral condyle is constructed by forming a radial section curve and a sagittal section curve of the posterior femoral condyle.

14. The method of claim 1, wherein the creating of the tibial component comprises:
    simulating a proximal tibia based on the collected anthropometric data, wherein the proximal tibia is simulated by: simulating a tibial plateau based on the collected anthropometric data.

15. The method of claim 14, wherein the simulated tibial plateau is constructed by forming a coronal section curve, a sagittal section curve, and an axial circumference of the tibial plateau.

16. A method of producing a knee replacement implant, the method comprising:
    defining a hip center, a knee center, an ankle center and a posterior femoral condylar axis of a lower limb;
    generating femoral geometric parameters and tibial geometric parameters, the femoral geometric parameters and the tibial geometric parameters being measured in relation to the hip center, the knee center, the ankle center and the posterior femoral condylar axis;
    collecting anthropometric data from a defined population using the femoral geometric parameters and the tibial geometric parameters; and
    creating a femoral component and/or a tibial component using the collected anthropometric data,
    wherein the generating of the femoral geometric parameters and the tibial geometric parameters comprises:
        building a plurality of different coordinate systems based on the hip center, the knee center, the ankle center and the posterior femoral condylar axis; and
        defining the femoral geometric parameters and the tibial geometric parameters by using the different coordinate systems, respectively; and
    wherein the ankle center is a gravity center of a cylinder fitted with an articular surface of a distal tibia of the lower limb.

* * * * *